(12) United States Patent
Ahimou et al.

(10) Patent No.: US 9,675,722 B2
(45) Date of Patent: Jun. 13, 2017

(54) BIOLOGICAL INDICATOR FOR MONITORING A LOW-TEMPERATURE STERILIZATION PROCESS

(71) Applicant: 3M INNOVATIVE PROPERTIES COMPANY, St. Paul, MN (US)

(72) Inventors: Francois Ahimou, Woodbury, MN (US); Assumpta Bennaars-Eiden, Coon Rapids, MN (US); William E. Foltz, Cottage Grove, MN (US); Swarnalatha Swaminathan, Woodbury, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 14/770,218

(22) PCT Filed: Feb. 20, 2014

(86) PCT No.: PCT/US2014/017280
§ 371 (c)(1),
(2) Date: Aug. 25, 2015

(87) PCT Pub. No.: WO2014/133854
PCT Pub. Date: Sep. 4, 2014

(65) Prior Publication Data
US 2016/0000954 A1    Jan. 7, 2016

Related U.S. Application Data

(60) Provisional application No. 61/769,357, filed on Feb. 26, 2013.

(51) Int. Cl.
*A61L 2/28* (2006.01)
*C12Q 1/22* (2006.01)
*C12M 1/12* (2006.01)

(52) U.S. Cl.
CPC ............. *A61L 2/28* (2013.01); *C12M 37/06* (2013.01); *C12Q 1/22* (2013.01); *A61L 2202/13* (2013.01)

(58) Field of Classification Search
CPC ....................................................... A61L 2/28
See application file for complete search history.

(56) References Cited

U.S. PATENT DOCUMENTS 3,346,464 A    10/1967    Ernst
3,585,112 A     6/1971    Ernst
(Continued)

FOREIGN PATENT DOCUMENTS

EP    0 638 650    2/1995
GB    2 127 962    4/1984
(Continued)

OTHER PUBLICATIONS

Parekh "Dried tubes specimens: A simple and cost effective method for preparation of HIV proficiency testing panels and quality control materials for use in resource-limited settings." Journal of Virological Methods 163 (2010) 295-300).*

(Continued)

*Primary Examiner* — Robert Yamasaki
*Assistant Examiner* — Charles Zoltan Constantine (57) ABSTRACT

An article and method are provided for assessing the efficacy of a sterilization process. The article comprises an outer container having an interior volume; a dry source of measurable biological activity disposed in the interior volume; and an effective amount of a dry agent for neutralizing a sterilant compound; wherein both the source of measurable biological activity and the agent are in vapor communication with an environment outside the outer container. The method comprises exposing the article to a first sterilant and, option- (Continued)

ally, a second sterilant for a period of time and detecting the measurable biological activity.

17 Claims, 2 Drawing Sheets

(56) References Cited

U.S. PATENT DOCUMENTS

| | | | |
|---|---|---|---|
| 3,846,242 | A | 11/1974 | Ernst |
| 4,169,123 | A | 9/1979 | Moore et al. |
| 4,169,124 | A | 9/1979 | Forstrom et al. |
| 4,291,122 | A | 9/1981 | Orelski |
| 4,304,869 | A | 12/1981 | Dyke |
| 4,337,223 | A | 6/1982 | Kaye |
| 4,416,984 | A | 11/1983 | Wheeler, Jr. |
| 4,454,094 | A | 6/1984 | Björling et al. |
| 4,461,837 | A | 7/1984 | Karle et al. |
| 4,528,268 | A | 7/1985 | Andersen et al. |
| 4,643,876 | A | 2/1987 | Jacobs et al. |
| 4,717,661 | A | 1/1988 | McCormick et al. |
| 4,756,882 | A | 7/1988 | Jacobs et al. |
| 4,883,641 | A | 11/1989 | Wicks et al. |
| 5,073,488 | A | 12/1991 | Matner et al. |
| 5,223,401 | A | 6/1993 | Foltz et al. |
| 5,418,167 | A | 5/1995 | Matner et al. |
| 5,552,320 | A | 9/1996 | Smith |
| 5,739,004 | A | 4/1998 | Woodson |
| 5,795,730 | A | 8/1998 | Tautvydas |
| 5,801,010 | A | 9/1998 | Falkowski et al. |
| 6,015,706 | A | 1/2000 | Kim et al. |
| 6,329,207 | B1 | 12/2001 | Fricker |
| 6,355,448 | B1 | 3/2002 | Foltz |
| 6,387,648 | B1 | 5/2002 | Levi |
| 6,451,272 | B1 | 9/2002 | Fryer |
| 6,706,532 | B2 | 3/2004 | Vadgama |
| 6,953,549 | B2 | 10/2005 | Hill |
| 7,674,602 | B2 | 3/2010 | Kadurugamuwa |
| 2007/0292305 | A1 | 12/2007 | Dempsey et al. |
| 2008/0199355 | A1 | 8/2008 | Berentsveig et al. |
| 2009/0047176 | A1 | 2/2009 | Cregger et al. |
| 2010/0112677 | A1 | 5/2010 | Onishi et al. |
| 2011/0076192 | A1 | 3/2011 | Robitaille et al. |
| 2012/0149094 | A1 | 6/2012 | Smith et al. |

FOREIGN PATENT DOCUMENTS

| | | |
|---|---|---|
| WO | WO 92-04057 | 3/1992 |
| WO | WO 2012-088064 | 6/2012 |
| WO | WO 2012-173756 | 12/2012 |

OTHER PUBLICATIONS

Ates "Plasma catalase activity and malondialdehyde level in patients with cataract" Eye (2004), 18, 785-788.*
Teerlink "Plasma Amino Acids Determined by Liquid Chromatography within 17 minutes" Clinical Chemistry 40(2), 245-249 (1994).*
Bagyan, I. et al.; "The katX Gene, Which Codes for the Catalase in Spores of Bacillus subtilis, Is a Forespore-Specific Gene Controlled by $\sigma^F$, and KatX Is Essential for Hydrogen Peroxide Resistance of the Germinating Spore";Journal of Bacteriology; vol. 180, No. 8; 1998; pp. 2057-2062.
Checinska, A. et al.; "Protection of Bacillus pumilus Spores by Catalases"; American Society for Microbiology; 2012; 40 pgs.
Conviser, S.; "The Future of Ethylene Oxide Sterilization"; 2003; 3 pgs.
Cortezzo, D.E. et al.; "Treatment with oxidizing agents damages the inner membrane of spores of Bacillus subtillis and sensitized spores to subsequent stress"; Journal of Applied Microbiology; vol. 97; 2004; pp. 838-852.
Destrez, P.; "Letters to the Editor—Reply to Fu et al.: Efficacy, efficiency and safety aspects of hydrogen peroxide vapour and aerosolized hydrogen peroxide room disinfection systems" Journal of Hospital Infection; vol. 82; 2012; 1 pg.
Espigares, E. et al.; "Efficacy of some neutralizers in suspension tests determining the activity of disinfectants"; Journal of Hospital Infection; vol. 55; 2003; pp. 137-140.
Fu, T. et al.; "Efficacy, efficiency and safety aspects of hydrogen peroxide vapour and aerosolized hydrogen peroxide room disinfection systems"; Journal of Hospital Infection; vol. 80; 2012; pp. 199-205.
Jordan, S. et al.; "Inactivation of Glutaraldehyde by Reaction with Sodium Bisulfite"; Journal of Toxicology and Environmental Health; vol. 47, No. 3; 1996; pp. 299-309.
Leung, H.; "Review—Ecotoxicology of Glutaraldehyde: Review of Environmental Fate and Effects Studies"; Ecotoxicology and Environmental Safety; vol. 49; 2001; pp. 26-39.
Milton, N.; "Homocysteine Inhibits Hydrogen Peroxide Breakdown by Catalase"; The Open Enzyme Inhibition Journal; vol. 1; 2008; pp. 34-41.
Peeters, J.E. et al.; "Effect of Disinfection of Drinking Water with Ozone or Chlorine Dioxide on Survival of Cryptosporidium parvum Oocysts"; Applied and Environmental Microbiology; vol. 55, No. 6; 1989; pp. 1519-1522.
Pottage, T. et al.; "Meticillin-resistant Staphylococcus aureus is more resistant to vaporized hydrogen peroxide than commercial Geobacillus stearothermophilus biological indicators"; Journal of Hospital Infection; vol. 80; 2012; pp. 41-45.
Przybylo, M. et al.; "UK laboratory diagnosis of Clostridium difficile infection: in a state of transition, confusion, or both?"; Letters to the Editor; Journal of Hospital Infection; vol. 80; 2012; pp. 273-274.
Shintani, H. et al.; "Gas plasma sterilization of microorganisms and mechanisms of action (Review)"; Experimental and Therapeutic Medicine; vol. 1; 2010; pp. 731-738.
Young, S.B. et al.; "Mechanisms of Bacillus subtilis spore resistance to and killing by aqueous ozone"; Journal of Applied Microbiology; vol. 96; 2004; pp. 1133-1142.
Web page entitled "REVOX® Technology Evolution—Sterilizing Agent Development"; from MEDIVATORS; [retrieved from the internet on Feb. 25, 2013]; URL http://www.medivators.com/products/revox-contract-sterilization-services/revox-technology.

* cited by examiner

BIOLOGICAL INDICATOR FOR MONITORING A LOW-TEMPERATURE STERILIZATION PROCESS

CROSS REFERENCE TO RELATED APPLICATIONS

This application is a national stage filing under 35 U.S.C. 371 of PCT/US2014/017280, filed Feb. 20, 2014, which claims priority to U.S. Provisional Patent Application No. 61/769,357, filed Feb. 26, 2013, the disclosure of which is incorporated by reference in its entirety herein.

BACKGROUND

Biological indicators (or "sterility indicators") are devices that are used to test the efficacy of sterilizers, such as those that are commonly used in hospitals for monitoring processes used to sterilize medical instruments, glassware, etc. The indicators typically include a source of microorganisms, a culture medium, and a detector to indicate the presence or absence of viable microorganisms. The culture medium may also serve as the detector, with formation of a cloudy suspension indicating growth of microorganisms. In practice, the source of microorganisms, typically an absorbent paper strip that has been impregnated with a predetermined quantity of live microorganisms is subjected to a sterilization process. Thereafter, the microorganism impregnated strip is placed in a sterile culture medium and incubated for a predetermined time at an appropriate temperature. At the end of the incubation period, the detector is used to determine whether any microorganisms survived the sterilization process. In some indicators, microorganism survival, which means the sterilization was incomplete, is shown by a change in color of the detector.

To simplify the sterilization test process and minimize the risk that external contamination would affect the test results, the elements of the biological indicator—microorganisms, culture medium, and detector—have sometimes been packaged in a way that permits the microorganism source, culture, and indicator to be combined without exposing the biological indicator to the non-sterile surroundings.

Low-temperature sterilization processes are often used to sterilize objects that may be damaged by the temperature and/or pressure used in steam sterilization processes. Biological indicators have been developed to monitor the efficacy of low-temperature sterilization processes that involve the use of ethylene oxide, hydrogen peroxide, or peracetic acid, for example. Recently, a sterilization system was developed to permit the operator to expose an object to two different low-temperature sterilants. One of the low-temperature sterilants comprises hydrogen peroxide and the other low-temperature sterilant comprises ozone.

SUMMARY

The present disclosure generally relates to biological indicator articles and methods to determine the efficacy of a sterilization process. In particular, the present disclosure relates to articles and methods to determine the efficacy of a sterilization process that utilizes one or more low-temperature sterilants. Typically, when two low-temperature sterilants are used in a sterilization process, each sterilant is used in an amount that is effective to reduce the number of microorganisms present in the sterilizer. Thus, theoretically, if one of the sterilant fails to sterilize the object completely (e.g., in a lumened portion of the object), the other sterilant should be sufficient to complete the sterilization of the object. The investigators have recognized the need for an article (e.g., a biological indicator) that can be used to distinguish the efficacy of a first quantity of a first sterilant used in a low-temperature sterilization process from the efficacy of second quantity of the first sterilant or a second quantity of a second sterilant that is used in the sterilization processes. In addition, the inventive article and method provides a solution to the problem of distinguishing the efficacy of one of the first quantity from the efficacy of the second quantity of the sterilization process.

Advantageously, the article of the present disclosure includes a feature that, when the article is exposed to a sterilization process utilizing a first quantity of an otherwise-effective amount of hydrogen peroxide (e.g., hydrogen peroxide vapor) under conditions effective to sterilize an object, protects a measurable biological activity from detrimental effects of the first quantity of hydrogen peroxide, even though exposure of the measurable biological activity to the first quantity otherwise would result in partial or total inactivation of the biological activity.

In one aspect, the present disclosure provides an article. The article can comprise an outer container having an interior volume, a first end comprising an opening, and a second end; a dry source of measurable biological activity disposed in the interior volume; and an effective amount of a dry agent for neutralizing hydrogen-peroxide, the agent being disposed in the interior volume. Both the source of measurable biological activity and the agent are in vapor communication with an environment outside the outer container. In any embodiment, the article further can comprise a closure coupled to the outer container, wherein the closure coupled to the outer container forms a passageway for vapor from the environment outside the outer container to pass to the interior volume.

In any of the above embodiments, the article further can comprise a layer that is permeable to hydrogen peroxide, wherein the layer is coupled to the outer container or the closure, wherein the layer is interposed between the source of measurable biological activity and the environment outside the outer container. In any of the above embodiments, the layer can be permeable to a second sterilant, wherein the second low temperature sterilant is a low-temperature sterilant other than hydrogen peroxide. In any of the above embodiments, the opening can comprise a tortuous path. In any of the above embodiments, the source of measurable biological activity can comprise an enzyme activity or a microorganism capable of reproducing. In any of the above embodiments, a portion of the measurable biological activity can be disposed in a first coating that is optionally disposed on a first substrate. In any of the above embodiments, the agent can be selected from a group consisting of catalase, a thiosulfate salt, a bisulfite salt, and L-methionine. In any of the above embodiments, a portion of the agent can be disposed in the first coating.

In another aspect, the present disclosure provides a method. The method can comprise processing an article using a process that comprises placing the article in a sterilization chamber, introducing into the chamber a first quantity of a first sterilant, exposing the article to the first sterilant for a period of time, and detecting a measurable biological activity. The first quantity of first sterilant can be suspected of comprising an effective amount of hydrogen peroxide. The article can comprise an outer container having an interior volume, a first end comprising an opening, and a second end; a dry source of the measurable biological activity disposed in the interior volume; and an effective amount of a dry agent for neutralizing hydrogen-peroxide, the agent being disposed in the interior volume. Both the source of the measurable biological activity and the agent are in vapor communication with an environment outside the outer container. In any embodiment, the method further can comprise introducing into the chamber a second quantity of a second sterilant and exposing the article to the second sterilant for a period of time.

In any embodiment of the method, the second quantity of second sterilant can be suspected of comprising hydrogen peroxide, wherein the second quantity is introduced into the chamber at a predetermined time after the first quantity is introduced into the chamber; or the second quantity of second sterilant can be suspected of comprising an effective amount of a sterilant other than hydrogen peroxide. In any of the above embodiments of the method, the second sterilant can comprise a gas plasma, ozone, peracetic acid, ethylene oxide or ions derived therefrom. In any of the above embodiments of the method, detecting the measurable biological activity comprises detecting an enzyme activity. In any of the above embodiments of the method, the second sterilant vapor or plasma can comprise ozone, peracetic acid, ethylene oxide or ions derived therefrom.

In yet another aspect, the present disclosure provides an article. The article can comprise an outer container having an interior volume, a first end comprising an opening, and a second end; a dry source of measurable biological activity disposed in the interior volume; and an effective amount of a dry agent for neutralizing a sterilant compound, the effective amount being disposed in the interior volume. Both the source of measurable biological activity and the agent are in vapor communication with an environment outside the outer container. In any embodiment, the article further can comprise a layer that is permeable to the sterilant compound, wherein the layer is coupled to the outer container, wherein the layer is interposed between the source of measurable biological activity and the environment outside the outer container. In any embodiment, the source of measurable biological activity can comprise an enzyme activity or a microorganism capable of reproducing. In any embodiment, the sterilant compound can comprise hydrogen peroxide The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably. Thus, for example, a closure comprising "a" window can be interpreted to mean that the closure can comprise "one or more" windows.

"Biological indicator" or "BI", as used herein, refer to an organism (e.g., a microorganism or spore) and/or biological activity (e.g., an enzyme activity) thereof, or an article comprising the organism and/or biological activity thereof, that is used to monitor the efficacy of a sterilization process.

"Self-contained biological indicator" or "SCBI", as used herein, refer to an article containing an organism and/or biological activity suitable for use as a biological indicator, along with components (e.g., nutrients, indicator reagents) necessary to detect the inactivation, or lack thereof, of the organism and/or biological activity.

Low-temperature sterilization process", as used herein, refers to a variety of sterilization processes that do not rely on exposing an object to be sterilized to steam under pressure (e.g., steam at a temperature greater than about 120 degrees Centigrade) for a period of time sufficient for the steam to cause sterilization of the object. Nonlimiting examples of low-temperature sterilization processes include processes that rely on exposing the object to compositions of ethylene oxide, hydrogen peroxide, chlorine dioxide, glutaraldehye, formaldehyde, or ozone to effect sterilization.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The features and advantages of the present invention will be understood upon consideration of the detailed description of the preferred embodiment as well as the appended claims. These and other features and advantages of the invention may be described below in connection with various illustrative embodiments of the invention.

The above summary of the present invention is not intended to describe each disclosed embodiment or every implementation of the present invention. The Figures and the detailed description which follow more particularly exemplify illustrative embodiments. Other features, objects and advantages will become apparent from the description and drawings, and from the claims.

BRIEF DESCRIPTION OF DRAWINGS

FIG. 1 is a cross-sectional side view of one embodiment of an article according to the present disclosure.

FIG. 2 is an exploded view the article of FIG. 1.

FIGS. 3A and 3B are exploded side views of two embodiments of a substrate having a source of measurable biological activity and an agent for neutralizing hydrogen peroxide disposed thereon.

FIG. 4 is a cross-sectional side view of an embodiment of a self-contained biological indicator having an inner container containing a detection medium according to the present disclosure.

FIG. 5 is an exploded view the article of FIG. 4.

While the above-identified drawing figures set forth several embodiments of the disclosure, other embodiments are also contemplated, as noted in the discussion. In all cases, this disclosure presents the invention by way of representation and not limitation. It should be understood that numerous other modifications and embodiments can be devised by those skilled in the art, which fall within the scope and spirit of the principles of the invention. The figures may not be drawn to scale.

DETAILED DESCRIPTION

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "connected" and "coupled" and variations thereof are used broadly and encompass both direct and indirect connections and couplings. Further, "connected" and "coupled" are not restricted to physical or mechanical connections or couplings. It is to be understood that other embodiments may be utilized and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure generally relates to methods and biological indicator articles for determining the efficacy of a sterilization process. In particular, the present disclosure relates to sterilization processes that include exposing an object to hydrogen peroxide (e.g., hydrogen peroxide vapor and/or plasma). In addition, the present disclosure relates to sterilization processes that include exposing an object to hydrogen peroxide and at least one other low-temperature sterilant (e.g., gas plasma, ozone, peracetic acid, glutaraldehyde, formaldehyde, ethylene oxide). Gas plasma sterilization of microorganisms is described by Shintani et al (GAS PLASMA STERILIZATION OF MICROORGANISMS AND MECHANISMS OF ACTION (REVIEW), 2010, Experimental and Therapeutic Medicine, 1:731-738), which is incorporated herein by reference in its entirety.

Exposing an object to a process that uses two distinct low-temperature sterilant treatments can provide an additional measure of protection in the event that one of the low-temperature sterilant treatments fails. The articles of the present disclosure may be used as biological indicators or self-contained biological indicators to monitor the efficacy of a sterilization process.

Biological indicators and chemical indicators used to determine the efficacy of a sterilization process are well known in the art. In conventional biological indicators, a biological activity, such as a test organism which is many times more resistant to the sterilization process employed than most organisms which would be present by natural contamination, is coated on a carrier and placed in a sterilizer along with the articles to be sterilized. After completion of the sterilization cycle, the carrier is incubated in nutrient medium to determine whether any of the test organisms survived the sterilization procedure. Growth of a detectable number of organisms normally takes a minimum of twenty-four hours. A number of so-called "self-contained biological indicators" (SCBI) have been described in the patent literature (e.g., U.S. Pat. Nos. 3,846,242; 4,717,661; 5,073,488; 5,223,401; 5,418,167; 5,739,004; 5,795,730; which are all incorporated herein by reference in their entirety.

In addition, enzyme activities have been used to determine the efficacy of a sterilization process. U.S. Pat. No. 5,073,488; which is incorporated herein by reference in its entirety; describes the usefulness of enzymes (e.g., beta-D-glucosidase, alpha-D-glucosidase, alkaline phosphatase, acid phosphatase, butyrate esterase, caprylate esterase lipase, myristate lipase, leucine aminopeptidase, valine aminopeptidase, chymotrypsin, phosphohydrolase, alpha-D-galactosidase, beta-D-galactosidase, alpha-L-arabinofuranosidase, N-acetyl-, 8-glucosaminidase, beta-D-cellobiosidase, alanine aminopeptidase, proline aminopeptidase, tyrosine aminopeptidase, phenylalanine aminopeptidase, beta-D-glucuronidase, and a fatty acid esterase) as biological indicators for sterilization processes.

The investigators have found that currently-available biological indicators may not be suitable to distinguish the efficacy of an individual low-temperature sterilant treatment when an object is exposed to a sterilization process that includes exposing the object to a plurality of chemically-distinct, low-temperature sterilant compounds or when the object is exposed to a sterilization process that includes discrete, sequential exposures to the same sterilant compound (e.g., hydrogen peroxide). In the situation where the object is exposed to a plurality of chemically-distinct, low-temperature sterilant compounds, this is because both of the two or more chemically-distinct, low-temperature sterilants individually may be capable of inactivating the test microorganism and/or enzyme activity of the biological indicator. Thus, if exposing the biological indicator to the first sterilant completely inactivates the biological indicator, it is not possible to determine whether exposure to the second sterilant has any sterilizing effect. In addition to recognizing this need (i.e., for a biological indicator that is capable of determining the efficacy of only one sterilant in a process that utilizes at least two chemically-distinct sterilants), the investigators also provide an article and method to fulfill the need.

In one aspect, the present disclosure provides an article for determining the effectiveness of a sterilization process. Although an article made according to the present disclosure can be used to modulate the resistance of a biological indicator to a sterilization process that utilizes a single low-temperature sterilant compound, the article is particularly useful for determining the effectiveness of one sterilant compound in a low-temperature sterilization process that utilizes two distinct (e.g., chemically-distinct) low-temperature sterilant compounds.

The article comprises an outer container having an interior volume, a first end comprising an opening, and a second end; a dry source of measurable biological activity disposed in the interior volume; and an effective amount of a dry agent for neutralizing a sterilant compound (e.g., hydrogen peroxide), the effective amount being disposed in the interior volume. Both the source of measurable biological activity and the agent are in vapor communication with an environment outside the outer container.

Figure 1:
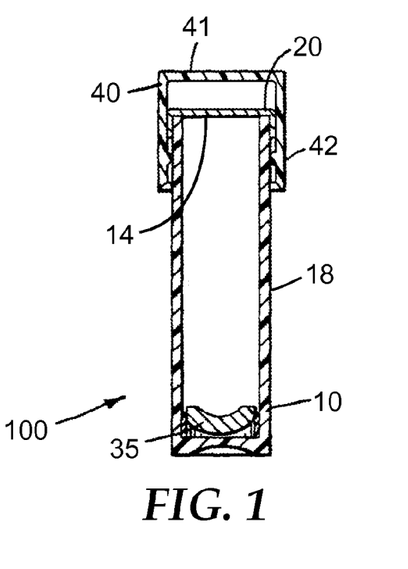
Figure 2:
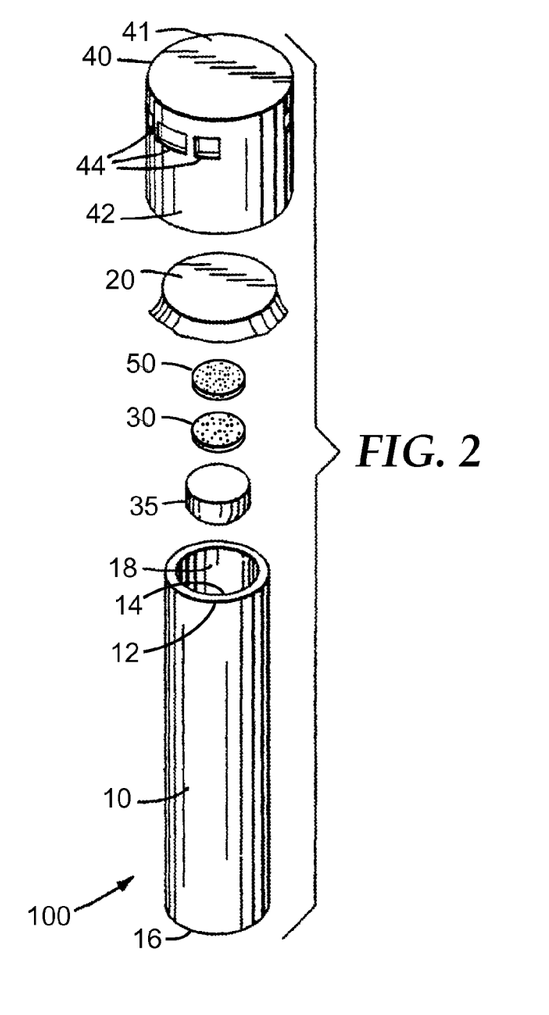

FIG. 1 shows a cross-sectional view and FIG. 2 shows an exploded perspective view of one embodiment of an article 100 according to the present disclosure. The article 100 comprises an outer container 10 having at least one sidewall 18 defining an interior volume, a first end 12 comprising an opening 14, and a second end 16. The opening 14 provides fluidic communication (e.g., vapor communication) between the interior volume of the outer container 10 and an environment (e.g., a gaseous environment) external to the outer container 10. In any embodiment, the opening 14 may comprise a tortuous pathway that is bacteria-impermeable, such as that described in U.S. Pat. No. 4,461,837, incorporated herein by reference, and in commonly assigned copending U.S. Pat. No. 4,883,641, issued Nov. 28, 1989.

The outer container 10 can have a variety of shapes including, for example, a right cylindrical shape as shown in FIGS. 1 and 2. The outer container 10 can be constructed of a variety of materials including, for example, glass and plastic. The outer container 10 can be fabricated using processes that are known in the art such as, for example, extrusion or molding processes. In any embodiment, the outer container 10 can be fabricated using a material that is liquid-impermeable, substantially non-gas absorptive and, optionally, optically transmissive (e.g., translucent or substantially transparent). Non-limiting examples of suitable materials include, but are not limited to, a variety of polyolefins, polyethylene, polypropylene, polycarbonate, polyamide, polymethylpentene, and polyester. In any embodiment wherein the article 100 comprises an outer container 10 with an inner container (described below) disposed therein, it is preferable the outer container 10 is sufficiently deformable so that a pressure-openable inner container is ruptured when the outer container 10 is deformed. In any embodiment, a breaker insert device (not shown) may be contained within outer container 10 and which may function to facilitate the breakage of an inner container (described below) when a downward axial force is applied to the closure 40 of article 100. Such a breaker insert device is taught in U.S. Patent Application Publication No. 2012/0149094, which is incorporated herein by reference in its entirety.

In any embodiment, the article 100 further comprises an optional closure 40 coupled (e.g., by friction fit) to the outer container 10. The closure 40 is comprised of a top 41 and depending sidewalls 42. The closure 40 restricts vapor communication (e.g., through the opening 14) between the environment and the interior volume of the container 10. The closure 40 has a hollow body open at the bottom, with the interior diameter of the closure 40 being about equal to the exterior diameter of the outer container 10, so that closure 40 may be frictionally engaged over the opening 14 of outer container 10. Cut within the sidewalls 42 are a plurality of windows 44. The windows 44 facilitate vapor communication (e.g., through the opening 14) between the environment and the interior volume of the container 10. Thus, the closure 40 coupled to the outer container 10 forms a passageway (e.g., via windows 44) for vapor or plasma from the environment outside the outer container to pass to the interior volume of the outer container 10. In any embodiment, the closure 40 coupled to the outer container 10 can form a passageway that comprises a tortuous path (not shown).

Although the illustrated embodiment of FIG. 2 shows windows 44 in the sidewall 42 of the closure 40, it is contemplated that, additionally or alternatively, the top 41 of the closure 40 can have one or more window extending therethrough (not shown).

When the article 100 is placed in a load to be sterilized, the closure 40 is positioned over the opening 14 in the outer container 10 in such a manner that the at least one exterior sidewall 18 of the outer container 10 does not block the windows 44. In such a position, steriliant vapor or plasma in the sterilizer may enter outer container 10 by flowing through windows 44. Upon completion of the sterilization cycle, the closure 40 may be fully engaged with the outer container 10 by depressing it to force the at least one sidewall 18 of the outer container 10 against the interior surface of the top 41 of the closure 40, thereby blocking windows 44. The interior of the outer container 10 is then sealed from the outside environment.

In any embodiment, the article 100 preferably further comprises an optional layer 20. The layer 20 is permeable to hydrogen peroxide vapor and/or hydrogen peroxide plasma. In any embodiment, the layer 20 is also permeable to vapor or plasma of at least one other steriliant compound that is used in a low-temperature sterilization process. In any embodiment, the layer 20 may be substantially impermeable to microorganisms (e.g., bacteria, spores, yeast, and/or mold). Non-limiting examples of the at least one other steriliant vapor or plasma include a gas plasma (e.g., a plasma of oxygen, nitrogen, helium, or argon), ozone, peracetic acid, and ethylene oxide. In any embodiment, the layer 20 may comprise a nonwoven sheet material such as a spunbonded olefin sheet material, for example.

Other suitable materials that are used to make layer 20 include fibrous materials such as cotton, glass wool, cloth, nonwoven webs made from polypropylene-, rayon, polypropylene/rayon, nylon, glass or other fibers, filter papers, microporous hydrophobic and hydrophilic films, open celled polymeric foams, and semi-permeable plastic films such as those described in U.S. Pat. No. 3,346,464. Fibrous or cellular materials are preferred because of the ease with which such materials transmit sterilizing gases. Preferred layer 20 materials include hydrophobic materials such as nylon web, microporous hydrophobic film, or glass fiber nonwoven web. Especially preferred is a microporous hydrophobic film, commercially available from Celanese Separations Products, Charlotte, N.C., under the trade name "CELGAR K-442 Microporous Film".

The layer 20 is disposed in the article 100 such that the layer 20 is interposed between a source of measurable biological activity (described below) and the environment exterior to the outer container 10. For example, the layer 20 may be press-fit into the opening 14 of the outer container 10 and held in position (e.g., by friction fit) or the layer 20 may extend over the opening 14 and held in place by a variety of means including, for example, a clamp, an elastic band, an adhesive, or a closure (discussed below). Alternatively, the layer 20 may be press-fit into the closure 40, or otherwise coupled to the closure (e.g., via an adhesive or clamp, not shown), and the closure 40 may be coupled to the outer container 10 via friction fit for example, thereby positioning the layer 20 between the interior volume of the outer container 10 and the environment external to the outer container as shown in FIGS. 1 and 2

In effect, the fibrous or cellular layer 20 may serve as a filter to prevent the penetration of bacteria and fungi into the outer container 10. Hence, layer 20 should have pore sizes no larger than about 0.5 microns (e.g., be capable of preventing the passage therethrough of particles having dimensions larger than about 0.5 microns). In any embodiment, the layer may be used in conjunction with the tortuous pathway described above.

The article 100 further comprises a source 30 of measurable biological activity. The source 30 of measurable biological activity is disposed in the interior volume of the outer container 10. In any embodiment, the source 30 of biological activity may be disposed in the outer container 10 in a position that places at least a portion of the layer 20, if present, between the source 30 of biological activity and the environment exterior to the outer container 10. Thus, because the opening 14; the closure 40; if present; and the layer 20, if present; permit the passage of a steriliant compound into the interior volume of the outer container 10 according to the present disclosure; the source 30 of measurable biological activity disposed in the outer container is in vapor communication with the steriliant compound that is present in the environment exterior to the outer container 10.

In the absence of a mitigating factor such as an agent for neutralizing the steriliant compound (e.g., an agent for neutralizing hydrogen peroxide) as described herein, the measurable biological activity in any article of the present disclosure may be susceptible to modulation (e.g., partial or total inactivation) when the source 30 of measurable biological activity is exposed to an environment comprising the steriliant compound (e.g., hydrogen peroxide vapor or hydrogen peroxide plasma). In any embodiment, in the absence of the mitigating factor, the measurable biological activity in any article of the present disclosure may be susceptible to irreversible modulation (e.g., partial or total inactivation)

when the source 30 of measurable biological activity is exposed to an environment comprising a vapor or plasma of the sterilant compound.

In addition, the measurable biological activity in any article of the present disclosure is susceptible to modulation (e.g., partial or total inactivation) when the source 30 is exposed to an environment comprising at least one sterilant vapor or plasma (e.g., a gas plasma, ozone, peracetic acid, or ethylene oxide) other than hydrogen peroxide. Preferably, at least a portion the measurable biological activity in any article of the present disclosure is irreversibly modulated (e.g., partially or totally inactivated) by exposing the source 30 of measurable biological activity to an atmosphere comprising at least one sterilant vapor or plasma other than hydrogen peroxide (e.g., a gas plasma, ozone, peracetic acid, or ethylene oxide). In a more preferred embodiment, exposing any article of the present disclosure that comprises a source of measurable biological activity to an efficacious sterilization process that uses a sterilant vapor or plasma (e.g., a gas plasma, ozone, peracetic acid, or ethylene oxide) other than hydrogen peroxide will irreversibly inactivate all of the measurable biological activity.

In any embodiment, the source 30 of measurable biological activity is substantially dry (e.g., a powder). In any embodiment, at least a portion (e.g., any portion up to and including a 100% portion) of the source 30 of measurable biological activity may be disposed in a first coating (e.g., a dry coating) on a surface. In any embodiment, the first coating can be applied to the surface as a liquid coating and subsequently dried using processes that are known in the art. The source 30 of measurable biological activity is disposed in the outer container 10 between the opening 14 and the second end 16. Preferably, the source 30 of measurable activity is disposed in the outer container 10 between the layer 20, when present, and the second end 16 in a position that places at least a portion of the layer 20 between the source 30 of biological activity and the opening 14. In any embodiment, the source 30 of biological activity is disposed at a position in the outer container 10 that is spaced apart from the opening 14 (e.g., the source of biological activity is positioned proximate the second end 16) so that a sterilant must penetrate substantially into the outer container 10 to contact the source 30 of biological activity. Thus, because the layer 20 is permeable to a sterilant vapor or plasma (e.g., hydrogen peroxide vapor or plasma), the source 30 of measurable biological activity is in vapor communication with sterilant vapor or plasma in the environment exterior to the outer container 10.

Optionally, the source 30 of measurable biological activity may be disposed on (e.g., coated on and/or adhered to) a surface of a first substrate 35. The first substrate 35 may take the form of a sheet, for example. The first substrate 35 is dimensioned to fit inside the outer container 10. The first substrate 35 may comprise a metal, glass, glass fibers, a membrane, a nonwoven material, a polymer (e.g., polypropylene, polyethylene, polyester), or a metal-coated polymer, for example. In some embodiments, the first substrate may comprise a cellulosic material, provided the cellulosic material does not substantially react with one or more of the sterilant compounds used in the sterilization process.

In any embodiment, the source 30 of measurable biological activity may comprise a test microorganism (e.g., a bacterium or a spore) capable of reproducing. Test microorganisms are conventionally used in a biological indicator (hereinafter, "BI") to monitor sterilization conditions. These conventionally-used test microorganisms are generally many times more resistant to the sterilization process being employed than most organisms encountered in natural contamination. The bacterial spore is recognized as the most resistant form of microbial life. It is the life form of choice in all tests for determining the sterilizing efficacy of sterilization devices, chemicals and processes. Spores from *Bacillus* and *Clostridia* species are the most commonly-used test microorganisms for monitoring sterilization processes that utilize saturated steam, dry heat, gamma irradiation and ethylene oxide.

In any embodiment, the source 30 of measurable biological activity may comprise a suspension of bacteria or spores that is coated and dried onto the first substrate 35. In any embodiment, at least a portion (e.g., any portion up to and including a 100% portion) of the source 30 of measurable biological activity is disposed on the first substrate 35. Alternatively, the source of measurable biological activity may be deposited directly into the container (e.g., on a wall 18 of the container proximate the second end, not shown). In these embodiments, the source of measurable biological activity may be deposited as a liquid suspension and subsequently dried using processes that are known in the art.

The measurable biological activity of a test microorganism (e.g., a bacterium or a spore) can be its ability to grow and reproduce. Thus, the biological activity may be detected (e.g., measured) by measuring, either directly or indirectly, a number of microorganisms. In some embodiments, the biological activity may be measured by measuring a metabolic activity (e.g., metabolic by-products such as organic acids, for example) associated with the presence of growing microorganisms. The production of organic acids by growing microorganisms permits the detection of the biological activity by detecting a drop in pH (e.g., by using a pH indicator that changes color when the pH drops).

Alternatively, or additionally, the source 30 of measurable biological activity may comprise an enzyme. The enzymes useful in the practice of the present invention include extracellular and intracellular enzymes, whose activity correlates with the viability of at least one test microorganism commonly used to monitor sterilization efficacy. By "correlates" it is meant that the enzyme activity, over background, can be used to predict future growth of the test microorganism. The enzyme must be one which, following a sterilization cycle which is sublethal to the test microorganism, remains sufficiently active to react with a substrate system for the enzyme, within twenty-four hours, and in preferred embodiments within eight hours or less, yet be inactivated or appreciably reduced in activity following a sterilization cycle which would be lethal to the test microorganism. Exemplary enzymes that can be used according to the present disclosure include alpha-D-glucosidase from spores of *Geobacillus stearothermophilus*, such as those commercially available as "ATCC 8005" and "ATCC 7953" from American Type Culture Collection, Manassas, Va., and beta-D-glucosidase from *Bacillus atrophaeus* (e.g., commercially available as "ATCC 9372" from American Type Culture Collection). Other suitable enzymes and methods for identifying suitable enzymes can be found in U.S. Pat. No. 5,073,488.

In any embodiment wherein the source of measurable biological activity is an enzyme, the source 30 of measurable biological activity may be: 1) a purified and/or isolated enzyme derived from an appropriate microorganism; 2) a microorganism to which the enzyme is indigenous or added by genetic engineering; or 3) a microorganism to which the enzyme has been added during sporulation or growth, such that the enzyme is incorporated or associated with the microorganism, e.g., an enzyme added to a spore during sporulation which becomes incorporated within the spore. Preferred microorganisms which may be utilized as a source of an enzyme useful in the practice of the present invention are bacteria or fungi in either the spore or vegetative state. Particularly preferred sources of enzyme include species of microorganisms from the genera *Bacillus, Geobacillus, Clostridium, Neurospora*, and *Candida*, for example.

Returning to the drawings, the article further comprises an agent 50 for neutralizing a sterilant compound (e.g., hydrogen peroxide). The agent 50 is disposed in the interior of the article (e.g., the interior volume of the outer container 10). Hydrogen peroxide is typically neutralized by decomposing it to water and oxygen. In this specification and the appended claims, with respect to hydrogen peroxide, "neutralize" and "decompose" are used interchangeably to refer to the process by which the hydrogen peroxide is inactivated. Suitable agents for neutralizing hydrogen peroxide include a variety of compositions including, for example, catalase, peroxidase, and other peroxide-neutralizing catalysts. A preferred composition is catalase, more preferably freeze-dried catalase powder. Suitable agents for neutralizing ozone include, for example, thiosulfate, metal ions (Cu+), and nitryl ions. Suitable agents for neutralizing formaldehyde include, for example, glycine. Suitable agents for neutralizing glutaraldehyde include for example, a bisulfite compound (see, for example, Susan L. P. Jordan (1996): INACTIVATION OF GLUTARALDEHYDE BY REACTION WITH SODIUM BISULFITE, Journal of Toxicology and Environmental Health, 47:3, 299-309); and H-W Leung (2001) ECOTOXICOLOGY OF GLUTARALDEHYDE: REVIEW OF ENVIRONMENTAL FATE AND EFFECTS STUDIES, Ecotoxicology and Environmental Safety, 49:26-39; which are both incorporated herein by reference in their entirety).

In any embodiment, the agent for neutralizing a sterilant compound may comprise a dry composition (e.g., a dry mixture) comprising a plurality of compounds (e.g., sodium bisulfite and sodium thiosulfate). The plurality of compounds may neutralize the same sterilant compound(s) and/or they may neutralize different sterilant compound(s). The use of liquid mixtures of compounds to neutralize high-level disinfectants is described, for example, in Espigares et al. (EFFICACY OF SOME NEUTRALIZERS IN SUSPENSION TESTS DETERMINING THE ACTIVITY OF DISINFECTANTS, J. Hospital Infection, 2003, 55:137-140), which is incorporated herein by reference in its entirety.

The agent 50 for neutralizing a sterilant compound optionally is mixed with a stabilizer (e.g., a powder), such as a sugar, a salt, other stabilizers well known in the art, or combinations thereof. The stabilizer not only extends the shelf life of the catalyst but also increases the quantity of powder to be used. This is desirable, since very little pure agent (e.g., and enzyme such as catalase) would be needed for an article of the present disclosure. Preferably, the stabilizer does not interfere with growth of a microorganism, if present, in the article 100. Other suitable agents for neutralizing hydrogen peroxide include a thiosulfate salt, a bisulfite salt, and L-methionine.

Metal catalysts, such as platinum, palladium, iron, etc, are also suitable hydrogen peroxide neutralizers. Preferably, the metal catalyst doesn't inhibit the growth of a microorganism, if present, in the article. Because high surface area may be desirable to facilitate rapid neutralization of hydrogen peroxide, the preferred form of a metal catalyst is either a fine powder of the metal or a coating of the metal on a fine ceramic powder.

The amount of agent 50 disposed in the container 10 should be sufficient to neutralize enough sterilant (e.g., hydrogen peroxide) to protect (i.e., prevent the killing or inactivation of) at least a portion of the measurable activity while the article 100 is exposed to typical sterilization process that utilizes an environment having enough of the sterilant (e.g., hydrogen peroxide) vapor or plasma to otherwise kill or inactivate all of the biological activity. The amount of agent used to neutralize hydrogen peroxide sterilant may vary depending upon whether the agent reacts with the hydrogen peroxide catalytically (i.e., one molecule of agent can react with more than one molecule of hydrogen peroxide) or stoichiometrically (i.e., one molecule of agent can react with only one molecule of hydrogen peroxide). The amount of neutralizing agent used in an article may also depend upon the hydrogen peroxide sterilization process in which it is used. The Examples herein provide guidance as to how much agent can be used and provide a simple procedure that can be used to test any given agent with any given sterilant (e.g., hydrogen peroxide) that is used in a low-temperature sterilization process.

In any embodiment, the agent 50 for neutralizing a sterilant compound is substantially dry (e.g., a powder). In any embodiment, at least a portion (e.g., any portion up to and including a 100% portion) of the agent 50 may be disposed in a second coating (e.g., a dry coating) on a surface. In any embodiment, the second coating can be applied to the surface as a liquid coating and subsequently dried using processes that are known in the art. The agent 50 is disposed in the outer container 10 between the layer 20 and the second end 16. The agent 50 is disposed in the outer container 10 in a position that places at least a portion of the layer 20 between the agent 50 and the opening 14. Thus, because the layer 20 is permeable to sterilant (e.g., hydrogen peroxide) vapor or plasma, the agent 50 is in vapor communication with sterilant vapor or plasma in the environment exterior to the outer container 10.

Figures 3A, 3B, 4, 5:
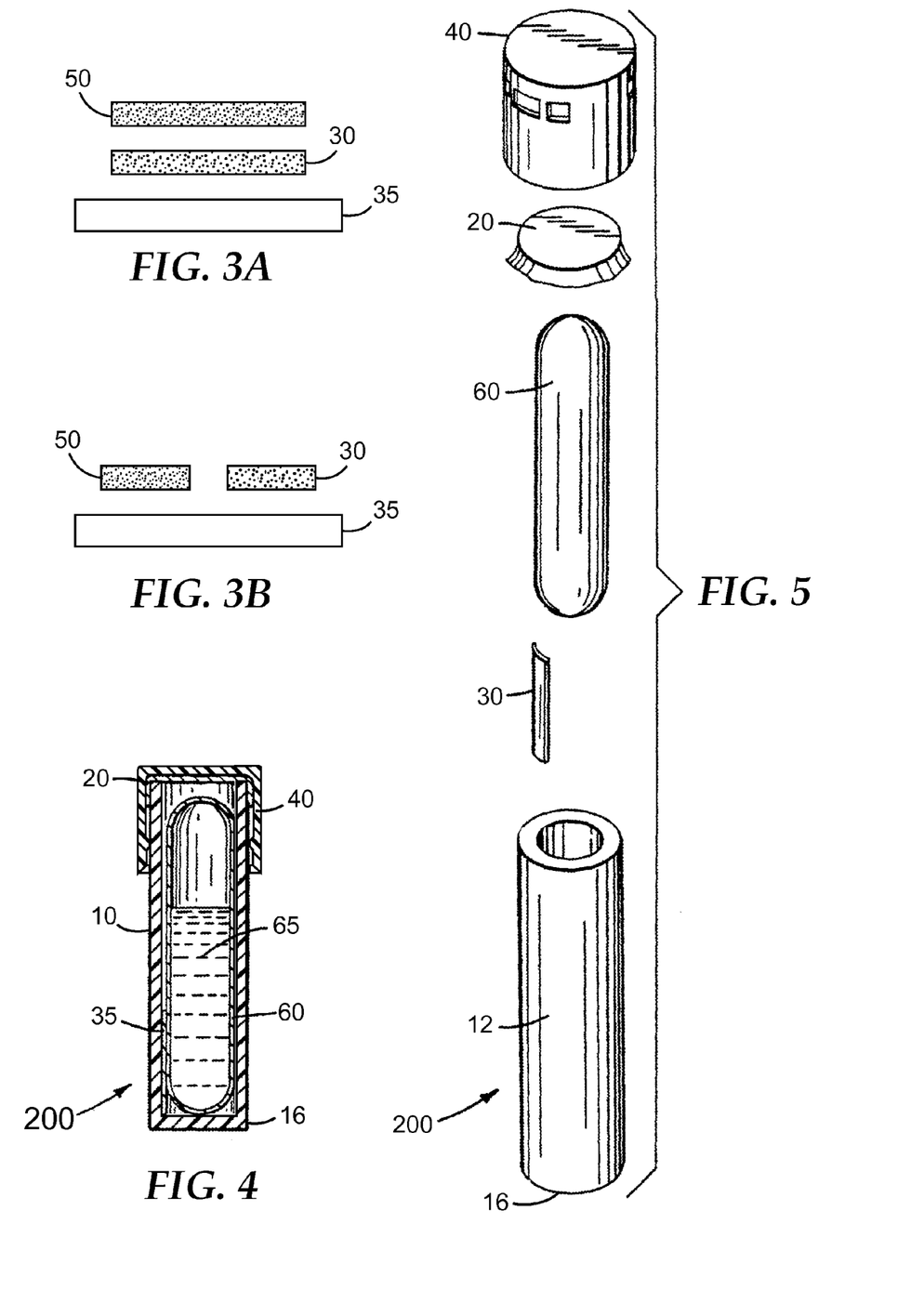

The agent 50 may be disposed in a variety of locations in the outer container 10. In any embodiment, at least a portion (e.g., any portion up to and including a 100% portion) of the agent 50 may be disposed on the first substrate 35, as shown in FIGS. 3A and 3B. Alternatively, the agent may be deposited directly into the container (e.g., on a wall of the container proximate the second end, not shown). In any embodiment, the agent may be deposited as a liquid suspension and subsequently dried using processes that are known in the art. Preferably, the agent 50 is disposed in the outer container 10 proximate the source 30 of measurable biological activity.

In any embodiment, the agent 50 is disposed in contact with the source 30 of measurable biological activity. For example, the source 30 of measurable biological activity may be disposed as a first coating on a first substrate 35 and the agent 50 may be disposed as a second coating that overlaps at least a portion of the source 30, as shown in FIG. 3A. Alternatively, the source 30 of measurable biological activity may be disposed as a first coating on a first substrate 35 and the agent 50 may be disposed as a second coating adjacent the first coating, as shown in FIG. 3A. In an alternative embodiment (not shown), the source of measurable biological activity is disposed as a first coating on a first substrate and the agent for neutralizing hydrogen peroxide is disposed as a second coating on a second substrate. In any embodiment, the second substrate may comprise the layer 20 described herein. In these embodiments, the second coating can be applied to a surface of the layer 20 facing the interior volume of the outer container 10. Thus, in any embodiment, the agent 50 for neutralizing a sterilant may be disposed proximate the opening 14 and the closure (discussed below), if present.

In any embodiment, the article further may comprise a nutrient (not shown) to facilitate the germination or outgrowth of a spore. In any embodiment, the article further may comprise an indicator (not shown) to indicate growth of a microorganism and/or indicate a presence of measurable enzyme activity. The nutrient and/or indicator may be disposed in the first coating or second coating described hereinabove.

In any embodiment, an article of the present disclosure may further comprise an inner container disposed in the outer container. FIGS. 4 and 5 show two views of one embodiment of an article 200 comprising an inner container according to the present disclosure. The article 200 comprises an outer container 10, layer 20, and closure 40, as described hereinabove. The article 200 also comprises a first substrate 35 on which the source of measurable biological activity (not shown) and agent for neutralizing a low-temperature sterilant (e.g., hydrogen peroxide), both described hereinabove, are disposed. In addition, the article 200 comprises an inner container 60 disposed in the outer container 10. The inner container 60 is disposed in the outer container 10 between the layer 20 and the second end 16. The inner container 60 contains a reagent 65 to facilitate the detection of the biological activity. In any embodiment, the reagent can be dissolved or suspended in an aqueous liquid.

The inner container 60 may contain an aqueous solution of an enzyme substrate and/or an aqueous nutrient medium. The inner container 60 is fabricated using material which is impermeable to gases and liquids and is capable of being opened upon the application of pressure thereto (i.e., "pressure openable") to permit the enzyme substrate and/or nutrient medium to enter the outer container 10. The inner container 60 is preferably of frangible material, such as glass; and is preferably snugly carried within the outer container 10 in coacting relationship therewith to permit breakage or crushing of the inner container 60 when the outer container 10 is deformed. In another embodiment (not shown), the inner container may be sealed with a plug such that the plug is expelled to release the contents of the inner container upon application of pressure. In still another embodiment (not shown), the closure may include an ampoule crushing device, as shown in U.S. Pat. No. 4,304,869, wherein the closure has tabs depending from the bottom of the closure device which, upon depression of the closure device, serve to crush the ampoule.

In an embodiment wherein the source of measurable biological activity is a microorganism and detection of the biological activity comprises detecting growth of the microorganism, the reagent may comprise a nutrient to facilitate the germination of a microbial spore and/or facilitate the growth of the microorganism. In an embodiment wherein the source of measurable biological activity is a microorganism (e.g., a microorganism from a germinated spore) and detection of the biological activity comprises detecting growth of the microorganism, the reagent may comprise an indicator (e.g., a pH indicator, a chromogenic enzyme substrate, a fluorogenic enzyme substrate) to facilitate the detection of a viable microorganism. Suitable reagents (i.e., nutrients, nutrient media, growth media, and indicators) for use in detecting a source of measurable biological activity comprising a microorganism are described, for example, in U.S. Pat. Nos. 3,346,464; 3,585,112; 4,291,122; 4,416,984; 4,528,268; 5,073,488; and 5,223,401; which are all incorporated herein by reference in their entirety.

In an embodiment wherein the source of measurable biological activity is an enzyme activity and detection of the biological activity comprises detecting the enzyme activity, the reagent of the present disclosure may comprise an enzyme substrate. Suitable indicators for detecting a source of measurable biological activity comprising an enzyme activity include, for example, a redox indicator, a chromogenic enzyme substrate, and a fluorogenic enzyme substrate. Non-limiting examples of suitable indicator reagents to detect an enzyme activity according to the present disclosure are disclosed in U.S. Pat. Nos. 5,073,488 and 6,355,448; which are incorporated herein by reference in their entirety.

In another aspect, the present disclosure provides a method for determining the effectiveness of a sterilization process. The method comprises processing the article of any one of the embodiments of the present disclosure using a sterilization process and detecting the measurable biological activity of the article. The article comprises a dry source of measurable biological activity and an effective amount of a dry agent for neutralizing a low-temperature sterilant compound (e.g., hydrogen peroxide), as described herein. The sterilization process comprises placing the article in a sterilization chamber; introducing into the chamber a first quantity of a first sterilant, wherein the first quantity of first sterilant is suspected of comprising an effective amount of hydrogen peroxide; and exposing the article to the first sterilant for a period of time.

The sterilization chamber can be any chamber suitable for conducting a low-temperature sterilization process. Non-limiting examples of suitable sterilization chambers have been described for low-temperature sterilization processes using ethylene oxide (see, for example, U.S. Pat. No. 4,337,223), hydrogen peroxide (see, for example, U.S. Pat. No. 6,953,549, which is incorporated herein by reference in its entirety), and ozone (see, for example, U.S. Patent Application Publication No. US 2011/0076192, which is incorporated herein by reference in its entirety).

Typically, processing an article in a sterilization processes comprises placing an article to be sterilized into a vessel and either introducing into the vessel or generating in the vessel an effective amount of the sterilant vapor or plasma (e.g., the first sterilant vapor or plasma or second sterilant vapor or plasma), thereby establishing in the vessel an environment (e.g., a gaseous and/or plasma environment) to which the article is exposed. Preferably, the article is held in the vessel under conditions suitable for an effective amount of the first sterilant vapor or plasma to sterilize the article. A person having ordinary skill in the art will recognize the suitable conditions. Suitable conditions may include, but are not limited to, the amount and type of material loaded into the vessel, the temperature of the vessel, the atmospheric pressure in the vessel, the relative humidity of the vessel, the length of time the article is held in the vessel, and a combination of two or more of the foregoing conditions.

The first sterilant can be any sterilant compound that is suitable for use in a low-temperature sterilization process as a vapor and/or plasma; the sterilant compound being a compound for which a corresponding neutralizer, which can be provided in the article in a substantially dry form, is identified. Nonlimiting examples of suitable first sterilant compounds include hydrogen peroxide and ozone.

The method comprises introducing into the sterilization chamber a first quantity of the first sterilant. Typically, the first quantity introduced into the chamber is a quantity suspected of being an effective amount of sterilant. An "effective amount" of sterilant, as used herein, refers to a quantity of sterilant compound introduced into a sterilization chamber (i.e., the sterilant is introduced into the chamber as a vapor-phase or plasma-phase and/or the sterilant is introduced into the chamber (e.g., as a liquid or solid) and is converted in the chamber into a vapor-phase and/or plasma-phase). The first quantity of the first sterilant is sufficient, according to typical parameters (e.g., temperature, exposure time, relative humidity or a combination of any two of the foregoing parameters) for using the first sterilant in a low-temperature sterilization process to reduce the number of viable test microorganisms (e.g., spores that are susceptible to the sterilant compound) in a biological indicator by at least a two-log reduction.

In any embodiment, the first sterilant comprises hydrogen peroxide. Sterilization processes that comprise a step of exposing an article to an environment comprising an effective amount of vapors or plasma of hydrogen peroxide are known in the art and are described, for example, in U.S. Pat. Nos. 4,169,123; 4,169,124; 4,643,876; and 4,756,882; which are all incorporated herein by reference in their entirety. In addition, commercial sterilizers (e.g., a STER-RAD NX sterilizer, available from Advanced Sterilization Products (ASP) of Irvine, Calif.; an AMSCO V-PRO 1 sterilizer, available from STERIS Corporation of Mentor, Ohio) include sterilization vessels and automated programs to expose an article to an environment comprising an effective amount of vapors or plasma of hydrogen peroxide.

Some of the automated programs for hydrogen peroxide sterilization processes provide the capability of introducing (e.g., in a generally continuous manner) hydrogen peroxide vapor (VHP) into the sterilization chamber until the concentration of the VHP reaches a predetermined value. The amount of VHP in the chamber can be estimated by measuring the pressure in the chamber as the VHP is introduced. Other automated programs provide the capability of introducing at least two discrete quantities of hydrogen peroxide at separate times into the chamber. Thus, in any embodiment, the method further can comprise introducing into the chamber a second quantity of a second sterilant, wherein the second sterilant comprises hydrogen peroxide. The first introduction of hydrogen peroxide introduces an effective amount into the chamber and a subsequent injection of hydrogen peroxide replenishes the vapor hydrogen peroxide that may have depleted due to condensation, degradation, and/or interaction with materials (including microorganisms) present in the load that is being treated and, thus, ensuring the efficacy of the sterilization process. In any embodiment, the second quantity can be suspected of comprising an effective amount of hydrogen peroxide.

Processing the article according to the method comprises exposing the article to the first sterilant for a period of time. A person having ordinary skill in the art will recognize, in order to decontaminate or sterilize an object (e.g., the article of the present disclosure), the efficacy of the process depends on the quantity of sterilant (e.g., the concentration of sterilant in the sterilization chamber), the length of time to which the object is exposed to the sterilant, and may depend upon other factors such as, for example, the temperature of the load and/or the chamber, relative humidity, and the amount and/or type (e.g. absorbent property, relative to the sterilant) of material present in the sterilization chamber. The Examples below provide general guidance for a typical process; however the parameters can be varied according to the desired result, as is well known by a person having ordinary skill in the art.

As discussed above, in any embodiment, a method of the present disclosure comprises introducing into the chamber a second quantity of a second sterilant. The second sterilant can be introduced into the chamber as a vapor or plasma or, alternatively, can be transformed in the chamber into a vapor or plasma form. In any embodiment, the second sterilant comprises a sterilant compound other than hydrogen peroxide. Suitable second sterilants include, but are not limited to, a gas plasma, ozone, chlorine dioxide, peracetic acid, ethylene oxide or ions derived therefrom. In any embodiment of the method, the second quantity can be suspected of comprising an effective amount of second sterilant.

Sterilization processes that comprise a step of exposing an article to an environment comprising an effective amount of ozone are known in the art and are described, for example, in PCT Patent Publication No. WO 92/04057, which is incorporated herein by reference in its entirety. Sterilization processes that comprise a step of exposing an article to an environment comprising an effective amount of vapor-phase peracetic acid also are known in the art and are described, for example, in PCT Patent Publication No. WO 2012/173756, which is incorporated herein by reference in its entirety. Sterilization processes that comprise a step of exposing an article to an environment comprising an effective amount of gaseous ethylene oxide also are known in the art (see, for example, U.S. Pat. No. 4,337,223, and U.S. Patent Application Publication No. US 2007/0292305, which are incorporated herein by reference in their entirety).

Recently, sterilizers that are capable exposing an article to two different types of sterilant vapors and/or plasmas have been developed. An exemplary sterilizer with the capability of exposing an article to two distinct sterilant compositions is described in U.S. Patent Application Publication No. 2011/0076192, which is incorporated herein by reference in its entirety. A commercial sterilizer (3M OPTREOZ 125-Z Sterilizer, or its equivalent, available from TS03 of Quebec City, Canada) is capable of introducing into a sterilization chamber a first quantity of a first sterilant (e.g., vapor-phase hydrogen peroxide) and a second quantity of a second sterilant (e.g., ozone) in order to sterilize the article. Thus, processing an article using a sterilization process according to the present disclosure can comprise placing the article into a sterilization vessel (e.g., a sterilization vessel similar to the 3M OPTREOZ 125-Z Sterilizer) that is adapted to expose the article to two distinct sterilants.

According to any embodiment of the method of the present disclosure, after the article has been processed (e.g., exposed to the first sterilant and/or second sterilant for a period of time), the measurable activity is detected. The procedure used to detect the measurable activity will vary according to the nature of the source of measurable biological activity and the components present in the article.

For example, when the source of measurable biological activity comprises a viable microorganism (e.g., a bacterium, a yeast, or a spore), detecting the measurable biological activity can comprise using a culture medium to culture the microorganism. In these embodiments, detecting the measurable biological activity may comprise incubating the source of biological activity in contact with the culture medium for a period of time. A person having ordinary skill in the art will recognize the incubation temperature is selected according to the typical requirements of the particular microorganism being cultured. For example, a spore of *Bacillus atrophaeus* may be incubated at a temperature around 37 degrees C., whereas a spore of *Geobacillus stearothermophilus* may be incubated at a temperature around 56 degrees C.

The microorganism can be cultured in the article (e.g., by adding a suitable culture medium to the article after the sterilization process or by rupturing the inner container to release into the outer container a suitable culture medium and/or indicator reagent contained in the inner container). A person having ordinary skill in the art will recognize a variety of methods to detect a plurality of microorganisms in a culture medium. The methods include, but are not limited to, using a chromogenic or fluorogenic enzyme substrate to observe an enzymatic reaction associated with the viable microorganism, using a chromogenic or fluorogenic redox indicator to observe and oxidation or reduction reaction associated with the viable microorganism, using a pH indicator to observe the production of an acidic or basic metabolite produced by a viable microorganism.

The types of nutrient media usefully employed in the present invention are widely known in the art. Examples of preferred nutrient media are aqueous solutions of soybean-casein digest broth, fluid thioglycollate and Dextrose Tryptone (Difco Laboratories, Inc.) A modified tryptic soy broth base, without glucose, is especially preferred. To avoid contamination, such aqueous nutrient media normally is sterilized after having been placed in the inner container. Commonly known microbial growth indicators, which change color in the presence of viable microorganisms, are preferably present in at least one of the containers. The growth indicator material preferably is soluble in, and imparts color (upon microorganism growth) to, the aqueous nutrient medium so that a change in color may be easily observed through the translucent walls of the outer container. In addition, the growth indicator material is preferably selected so that it will not interfere with the color or luminescence of the enzyme-modified product. Growth indicator materials which may be employed in the present invention are well known to the art and include pH-sensitive dye indicators (such as bromothymol blue, bromocresol purple, phenol red, etc.), oxidation-reduction dye indicators (such as methylene blue, etc.). Such materials commonly undergo changes in color in response to a phenomenon of microorganism growth, such as changes in pH, oxidation-reduction potentials, etc.

Observing a reaction associated with a viable microorganism can comprise using an instrument to detect the reaction. Observing a reaction associated with a viable microorganism can comprise using an instrument to measure a product (e.g., a chromogenic or fluorogenic product) of the reaction. In any embodiment, detecting the measurable biological activity may comprise detecting the absence of the measurable biological activity.

When the source of measurable biological activity comprises an enzyme activity, detecting the measurable biological activity can comprise using an enzyme substrate system (e.g., comprising a luminescent enzyme substrate, a chromogenic enzyme substrate or a fluorogenic enzyme substrate) to detect the measurable biological activity. In these embodiments, detecting the measurable biological activity may comprise incubating the source of biological activity in contact with the enzyme substrate for a period of time.

In the context of this application, an enzyme substrate system is by definition a substance or mixture of substances acted upon by an enzyme and converted into an enzyme-modified product. In general, the enzyme modified product is a luminescent, fluorescent, colored or radioactive material. However, the enzyme substrate system can consist of a compound which when reacted with the enzyme, will yield a product which will react with an additional compound or composition to yield a luminescent, fluorescent, colored or radioactive material. Preferably, where the substrate system is to be included in the indicator device during sterilization, the substrate must not spontaneously break down or convert to a detectable product during sterilization or incubation. For example, in devices used to monitor a process using hydrogen peroxide vapors or plasma and ozone vapors or plasma, the components of the substrate system should be stable at temperatures between about 20° and 80° C. Preferably also, where the enzyme substrate system is to be stored in and/or used with conventional growth media, it should be stable (e.g., not substantially spontaneously hydrolyze) when in contact with the growth media.

Detecting a measurable biological activity that comprises an enzyme activity comprises observing a product of the reaction catalyzed (e.g., directly or indirectly) by the enzyme activity. Observing a product of a reaction catalyzed by the enzyme activity can comprise using an instrument to detect the product. Observing a product of a reaction catalyzed by the enzyme activity can comprise using an instrument to measure the product (e.g., light, a colored product, or fluorescent product). In any embodiment, detecting the measurable biological activity may comprise detecting the absence of the measurable biological activity.

A preferred method of monitoring a fluorescent product of a measurable biological activity of the present disclosure is to use a fluorimeter designed specifically (e.g., configured to be operably coupled to the outer container) for the articles of the present disclosure. A fluorimeter eliminates the subjective interpretation encountered when attempting to visually differentiate between low levels of a fluorescent product and background fluorescence (e.g. due to components of a nutrient medium, if present) or no fluorescence. A fluorimeter can be calibrated to detect a minimum amount of fluorescent product within a given incubation period.

A particularly preferred fluorimeter, designed for use with the devices of this invention, consists of a chamber designed to block ambient light while positioning the outer container of the article such that the source of measurable biological activity within the outer container can be illuminated with a 365 nm wavelength ultraviolet light, and a photodiode can be used detect any resultant fluorescence in the 460 nm wavelength region. The fluorimeter may be calibrated to detect a threshold amount of fluorescence to distinguish the presence of measurable biological activity.

The method of the present disclosure can be used to determine the effectiveness of a quantity of second sterilant used in a sterilization process that utilizes first and second sterilant compounds as described herein. Advantageously, this is possible whether the first and second sterilant compounds are the same compound or are different compounds. The agent for neutralizing a sterilant compound (e.g., a first sterilant compound such as hydrogen peroxide) prevents the first sterilant compound from inactivating (e.g., partially or totally inactivating) the source of measurable biological activity. Therefore, if the measurable activity is detected (e.g., at least a portion or all of the measurable activity is detected) after the article is exposed to both the first and second sterilant compounds, it can be concluded that the sterilization process, in general, and the quantity of second sterilant compound, in particular, were not effective to sterilize the article.

EXEMPLARY EMBODIMENTS

Embodiment A is an article, comprising:
an outer container having an interior volume, a first end comprising an opening, and a second end;
a dry source of measurable biological activity disposed in the interior volume; and an effective amount of a dry agent for neutralizing hydrogen peroxide, the agent being disposed in the interior volume;

wherein both the source of measurable biological activity and the agent are in vapor communication with an environment outside the outer container.

Embodiment B is the article of Embodiment A, further comprising a closure coupled to the outer container, wherein the closure coupled to the outer container forms a passageway for vapor or plasma from the environment outside the outer container to pass to the interior volume.

Embodiment C is the article of Embodiment A or Embodiment B, further comprising a layer that is permeable to hydrogen peroxide, wherein the layer is coupled to the outer container or the closure, wherein the layer is interposed between the source of measurable biological activity and the environment outside the outer container.

Embodiment D is the article of Embodiment C, wherein the layer is permeable to hydrogen peroxide and a second low-temperature sterilant, wherein the second low temperature sterilant is a low-temperature sterilant other than hydrogen peroxide.

Embodiment E is the article of any one of the preceding claims, wherein the opening or the passageway comprises a tortuous path.

Embodiment F is the article of any one of the preceding embodiments, wherein the measurable biological activity comprises an enzyme activity.

Embodiment G is article of any one of Embodiments A through E, wherein the measurable biological activity is a microorganism capable of reproducing.

Embodiment H is the article of Embodiment G, wherein the microorganism is an endospore.

Embodiment I is the article of any one of the preceding Embodiments, wherein the second sterilant is selected from a group consisting of a gas plasma, ozone, peracetic acid, and ethylene oxide.

Embodiment J is the article of any one of the preceding Embodiments, wherein a portion of the source of measurable biological activity is disposed in a first coating.

Embodiment K is the article of Embodiment J, wherein the article further comprises a first substrate, wherein the first coating is disposed on the first substrate.

Embodiment L is the article of any one of the preceding Embodiments, wherein the agent is selected from a group consisting of catalase, a thiosulfate salt, a bisulfite salt, and L-methionine.

Embodiment M is the article of any one of the preceding Embodiments, wherein a portion of the agent is disposed in the first coating.

Embodiment N is the article of any one of the preceding Embodiments wherein a portion of the agent is disposed in a second coating.

Embodiment O is the article of Embodiment N, wherein the article further comprises a second substrate, wherein a portion of the second coating is disposed on the second substrate.

Embodiment P is the article of Embodiment O, wherein the layer is the second substrate, wherein the second coating is disposed on or in the second substrate.

Embodiment Q is the article of any one of Embodiments N through P, wherein the second coating is proximate the first coating.

Embodiment R is the article of Embodiment Q, wherein a portion of the second coating overlays the first coating.

Embodiment S is the article of any one of Embodiments G through R, further comprising a nutrient to facilitate growth of the microorganism.

Embodiment T is the article of any one of the preceding Embodiments, further comprising an indicator capable of reacting with the source of measurable biological activity.

Embodiment U is the article of Embodiment S or Embodiment T, wherein the nutrient or the indicator is disposed in an inner container that is disposed in the outer container between the first end and the second end.

Embodiment V is a method, comprising:

processing the article of any one of the preceding Embodiments using a process that comprises:

placing the article in a sterilization chamber;

introducing into the chamber a first quantity of a first sterilant, wherein the first quantity of first sterilant is suspected of comprising an effective amount of hydrogen peroxide;

exposing the article to the first second sterilant for a period of time; and detecting the measurable biological activity.

Embodiment W is the method of Embodiment V, further comprising:

introducing into the chamber a second quantity of a second sterilant; and exposing the article to the second sterilant for a period of time.

Embodiment X is the method of Embodiment W, wherein the second quantity of second sterilant is suspected of comprising hydrogen peroxide, wherein the second quantity is introduced into the chamber at a predetermined time after the first quantity is introduced into the chamber.

Embodiment Y is the method of Embodiment W, wherein the second quantity of second sterilant is suspected of comprising an effective amount of a sterilant other than hydrogen peroxide.

Embodiment Z is the method of Embodiment X, wherein the second quantity is introduced into the chamber after the first quantity is introduced into the chamber.

Embodiment AA is the method of any one of Embodiments V through Z, wherein exposing the article to a first sterilant comprises exposing the article to the first sterilant under conditions suitable for efficacy of the first sterilant.

Embodiment BB is the method of any one of Embodiments V through AA, wherein exposing the article to a second sterilant comprises exposing the article to the second sterilant under conditions suitable for efficacy of the second sterilant.

Embodiment CC is the method of any one of Embodiments W through BB, wherein the second sterilant comprises a gas plasma, ozone, peracetic acid, ethylene oxide or ions derived therefrom.

Embodiment DD is the method of any one of Embodiments V through CC, wherein detecting the measurable biological activity comprises detecting an enzyme activity.

Embodiment EE is the method of any one of Embodiments V through DD, wherein detecting the measurable biological activity comprises detecting a pH change.

Embodiment FF is an article, comprising:

an outer container having an interior volume, a first end comprising an opening, and a second end;

a dry source of measurable biological activity disposed in the interior volume; and an effective amount of a dry agent for neutralizing a low-temperature sterilant compound, the effective amount being disposed in the interior volume;

wherein both the source of measurable biological activity and the agent are in vapor communication with an environment outside the outer container.

Embodiment GG is the article of Embodiment FF, further comprising a layer that is permeable to the low-temperature sterilant compound, wherein the layer is coupled to the outer container, wherein the layer is interposed between the source of measurable biological activity and the environment outside the outer container.

Embodiment HH is the article of Embodiment FF, wherein the opening comprises a tortuous path.

Embodiment II is the article of any one of Embodiments FF through HH, wherein the source of measurable biological activity comprises an enzyme activity.

Embodiment JJ is the article of any one of Embodiments FF through HH, wherein the source of measurable biological activity is a microorganism capable of reproducing.

Embodiment KK is the article of any one of Embodiments FF through JJ, wherein the low-temperature sterilant compound comprises hydrogen peroxide.

Advantages and embodiments of this disclosure are further illustrated by the following examples, but the particular materials and amounts thereof recited in these examples, as well as other conditions and details, should not be construed to unduly limit this disclosure. All materials are commercially available or known to those skilled in the art unless otherwise stated or apparent.

EXAMPLES

Sterilizer Systems and Sterilization Cycle Parameters.

The biological indicators (BIs) described in the Examples below, were exposed to sterilization cycles using hydrogen peroxide sterilization with a STERRAD NX sterilizer (available from Advanced Sterilization Products (ASP) of Irvine, Calif.) and the 3M OPTREOZ 125-Z Sterilizer (available from TS03 of Quebec City, Canada). The sterilant concentration and exposure time was varied. In the STERRAD NX sterilizer, the BIs were exposed to a standard ("full") cycle and a 3 minute ("half") cycle exposure. The half cycle used a smaller quantity of the sterilant, hydrogen peroxide, injected into the chamber. In the 3M OPTREOZ 125-Z sterilizer, some of the BIs were exposed to a full "Cycle 2" which used hydrogen peroxide followed by ozone, and some of the BIs were exposed to a 11.84 Torr (1.58 kPa) hydrogen peroxide-only cycle. The descriptions of the STERRAD NX cycles and OPTREOZ cycles are listed in Tables 1 and 2 below.

TABLE 1

STERRAD NX sterilizer: Standard cycle and 3 minute exposure cycles

| Cycle stages | Controlled parameter | Standard Cycle | 3 min Half Cycle |
|---|---|---|---|
| 1) Delivery | Volume of 59% $H_2O_2$ solution admitted into the sterilizer | 1.8 mL | 1.0 mL |
| 2) Exposure | Exposure to $H_2O_2$ | 3 minutes | 3 minutes |
| Number of phases | | 2 | 1 |
| Approx. cycle duration (empty chamber) | | 28 minutes | 14 minutes |

TABLE 2

OPTREOZ 125 Z sterilizer: Cycle 2 and hydrogen peroxide only cycles

| Cycle stages | Controlled parameter | Cycle 2 | Hydrogen Peroxide only |
|---|---|---|---|
| 1) Vacuum | Pressure | 1 Torr (0.133 kPa) | 1 Torr (0.133 kPa) |
| 2) $H_2O_2$ Injection | $P_v$ of 50% $H_2O_2$ solution admitted | 19 Torr (2.53 kPa) | 11.84 Torr (1.58 kPa) |
| 3) $O_3$ Injection | Ozone dose injected | 10 mg/L | 0 mg/L |
| 4) Exposure | Duration | 5 minutes | 0 minutes |
| Number of phases | | 2 | 1 |
| Approx. cycle duration (empty chamber) | | 56 minutes | Less than 50 minutes |

Examples 1-5

The effect of catalase, as an agent for neutralizing hydrogen peroxide, on protecting spores from exposure to a hydrogen peroxide sterilization process was evaluated by positioning catalase at different locations inside example biological indicators. Lyophilized catalase powder from bovine liver, available from Sigma Aldrich, St. Louis, Mo., was used in the examples described below. Commercially available 3M ATTEST 1274 Biological Indicators and 3M ATTEST 1292 Rapid Readout Biological Indicators, were modified by the addition of catalase as follows: Ten sample biological indicators (BIs) were prepared for each of Examples 1-4 and 12 samples were prepared for Example 5. After the Examples 1-5 were prepared as described below, they were subjected to the STERRAD NX sterilizer standard cycle, described in Table 1, above. Table 3 below shows the results of the sterilized biological indicators as a ratio of positive/total BIs evaluated. A positive result implies that the catalase enzyme activity was effective in preventing the hydrogen peroxide sterilant from killing all the spores in the BI.

The Biological Indicator article used in Example 1 was prepared by first disassembling several 3M ATTEST 1274 Biological Indicators, available from 3M Company of St. Paul, Minn. The component parts of the 1274 Biological Indicators included an outer container (sleeve) with an opening, a sealed glass inner container (ampoule) containing a nutrient medium and an indicator for detecting biological activity, a first substrate comprising a small circular metal coupon containing *Geobacillus stearothermophilus* spores coated thereon, a blue colored cap filter material (i.e., the "layer", as described hereinabove), and a closure. Additionally, a 1.27 cm diameter piece of DUPONT brand TYVEK material was cut from a roll of 12407 TYVEK® Roll with STERRAD® Chemical Indicator, available from Advanced Sterilization Products (ASP) of Irvine, Calif. The circular cut piece of TYVEK material intentionally did not include the chemical indicator, but was simply used as a second substrate material on which the catalase was disposed. This TYVEK second substrate was spiked with a 10 mg/mL aqueous solution of catalase, to deliver 200 μg of catalase per BI. The catalase spiked TYVEK material was allowed to dry. The modified Biological Indicator of Examples 1-5 was made by reassembling the parts: first placing the spore-coated first substrate into the bottom of the outer container; next the inner container containing the nutrient medium and the indicator for detecting biological activity was placed into the outer container; and then the catalase spiked second-substrate was placed into the outer container. Finally, the closure was friction-fitted over the opening of the outer container. Thus, in this Example, the blue colored cap filter material (i.e., the "layer", as described herein) was replaced with the catalase spiked TYVEK material.

Example 2 was prepared in the same manner as Example 1 with the exception that a different second substrate material was used. Instead of the TYVEK material cut from a roll of 12407 TYVEK® Roll with STERRAD® Chemical Indicator, a different non-woven web material was used, which consisted of 95/5 PP/rayon web material. The 95/5 PP/rayon material was a carded non-woven web made of 95% polypropylene (single component) fibers and 5% LENZING (single component) rayon fibers at a basis weight of 135 gsm and carded through a two roll calendering method at 160° C. with one smooth roll and the other roll with an approximately 17% point bond pattern. The rayon fibers were LENZING VISCOSE 1.7 dtex, 39 mm cut length, bright raw white rayon fibers (Lenzing Fibers; New York, N.Y. The polypropylene fibers were FIBERVISIONS T-133/HY-Entangle 1.7 dtex polypropylene fibers (FiberVisions Corporation; Duluth, Ga.). Additionally, Example 2 was spiked at 3 levels of catalase, to achieve: 20 µg, 100 µg, and 200 µg of catalase per BI for Examples 2-1, 2-2 and 2-3, respectively. The catalase spiked second substrate material was allowed to dry and then the BIs were reassembled.

Example 3 was prepared in the same manner as Example 2, using the 95/5 PP/Rayon web material, as the second substrate material. However, in Example 3 when the components of the 3M ATTEST 1274 BI were reassembled, after the spore-coated first substrate was placed into the bottom of the outer container; next the catalase spiked second substrate was placed over the spore-coated first substrate; then the inner container containing the nutrient medium and the indicator for detecting biological activity was inserted, followed by the blue colored cap filter material. Finally, the closure was friction-fitted onto the outer container. Thus, in Example 3 the catalase was positioned in closer proximity to the spores, compared to Examples 1 and 2. Additionally, Example 3 was spiked at 2 levels of catalase, to achieve: 20 µg, and 200 µg of catalase per BI for Examples 3-1, and 3-2, respectively. The catalase-spiked second substrate was allowed to dry and then the BIs were reassembled.

Example 4 was prepared in the same configuration as Example 3, in that the catalase-coated second substrate was positioned in between the spore-coated first substrate and the inner container containing the growth medium and indicator. However, Example 4 was prepared by using 3M ATTEST 1292 Rapid Readout Biological Indicator; instead of the 3M ATTEST 1274 BI. The 3M ATTEST 1292 Rapid Readout Biological Indicator has the same number of components, oriented the same way, as the 1274 BI. However, the cap filter material (i.e., the "layer", as described herein above) in the 3M ATTEST 1292 Rapid Readout BI is a white polypropylene (PP) meltblown web material. That PP web filter material was taken from a different 3M ATTEST 1292 Rapid Readout BI, and used as the catalase-coated second substrate material. The aqueous catalase stock solution was spiked onto this second substrate material to achieve a loading of about 200 µg of catalase per BI, allowed to dry and then reassembled.

Example 5 was prepared by first disassembling several 3M ATTEST 1274 Biological Indicators, then spiking aqueous catalase stock solution directly onto the spores coated on the metal first substrate, allowed to dry at room temperature conditions and then reassembling the biological indicators.

Reference Example 1

Reference Example 1, a control for Example 1 was prepared in exactly the same manner as Example 1, except that the TYVEK second substrate material was not spiked with catalase.

Reference Example 2

As with Reference Example 1, a control designated Reference Example 2, was prepared by preparing a sample exactly like Example 2, but with no catalase spiked onto the 95/5 PP/Rayon web second substrate material.

Reference Example 3

As with Reference Examples 1 and 2, a control designated Reference Example 3, was prepared by preparing a sample exactly like Example 3, but with no catalase spiked on the 95/5 PP/Rayon web material.

Reference Example 4

Like the above Reference Examples, a control designated Reference Example 4 was prepared in exactly the same manner as Example 4, but without any catalase spiked on the second substrate material.

Reference Example 5

Like the above Reference Examples, a control designated Reference Example 5 was prepared in exactly the same manner as Example 5, but without any catalase spiked on the second substrate material.

TABLE 3

Location of Catalase as an Effect on Neutralization of Hydrogen Peroxide in Biological Indicators

| Example | Catalase Amount per BI | Second Substrate Material | Catalase-coated Second Substrate Location | Positive BI/Total BI's |
|---|---|---|---|---|
| Ref. Ex. 1 | 0 µg/BI | TYVEK | Near the Closure | 0/10 |
| Ex. 1 | 200 µg/BI | TYVEK | Near the Closure | 0/10 |
| Ref. Ex. 2 | 0 µg/BI | PP/Rayon | Near the Closure | 0/10 |
| Ex. 2-1 | 20 µg/BI | PP/Rayon | Near the Closure | 0/10 |
| Ex. 2-2 | 100 µg/BI | PP/Rayon | Near the Closure | 0/10 |
| Ex. 2-3 | 200 µg/BI | PP/Rayon | Near the Closure | 0/10 |
| Ref. Ex. 3 | 0 µg/BI | PP/Rayon | Above Spore Carrier | 0/10 |
| Ex. 3-1 | 20 µg/BI | PP/Rayon | Above Spore Carrier | 0/10 |
| Ex. 3-2 | 200 µg/BI | PP/Rayon | Above Spore Carrier | 6/10 |
| Ref. Ex. 4 | 0 µg/BI | PP Web | Above Spore Carrier | 0/10 |
| Ex. 4 | 200 µg/BI | PP Web | Above Spore Carrier | 10/10 |
| Ref. Ex. 5 | 0 µg/BI | None/Direct | Directly on spores | 0/12 |
| Ex. 5 | 200 µg/BI | None/Direct | Directly on spores | 10/12 |

Examples 6-9

The effect of different levels of various hydrogen peroxide-neutralizing agents on the resistance of spores to a hydrogen peroxide sterilization process was evaluated in Examples 6-9. Commercially available 3M ATTEST 1274 Biological Indicators were modified by the addition of various neutralizing agents as described below. For each group of samples, 4 similarly prepared biological indicators (BIs) were subjected to the same sterilization cycle. Table 4 below shows the results of the sterilized biological indicators of Examples 6-9 as a ratio of positive/total BIs evaluated. A positive result implies that the neutralizing agent was effective in preventing the hydrogen peroxide sterilant from killing all the spores in the BI.

Example 6 was prepared by first disassembling several 3M ATTEST 1274 Biological Indicators. Then, like Example 5, and amount of aqueous catalase solution was spiked directly onto the spores on the metal spore carrier coupon, to achieve 4 levels of catalase: 4 µg, 20 µg, 50 µg, and 100 µg catalase per BI. The catalase solution was allowed to dry and then the modified 3M ATTEST 1274 Biological Indicators were reassembled in their original configuration. Reference Example 6 was a control and, thus, had no catalase added.

Example 7 was prepared in the same manner as Example 6, except that sodium thiosulfate was used instead of catalase as the hydrogen peroxide-neutralizing agent. The sodium thiosulfate, ($Na_2S_2O_3$) anhydrous, ≥98.0%, was obtained from Sigma Aldrich Company of St. Louis, Mo. Four levels of sodium thiosulfate were spiked onto the spores: 20 µg, 100 µg, 200 µg and 2000 µg sodium thiosulfate per BI.

Example 8 was prepared in the same manner as Example 6, except that sodium bisulfite was used instead of catalase as the hydrogen peroxide-neutralizing agent. The sodium bisulfite, ($HNaO_3S$) reagent grade, was manufactured by BDH, and was obtained through VWR of Radnor, Pa. Four levels of sodium bisulfite were spiked onto the spores: 20 µg, 200 µg, 250 µg and 2500 µg sodium bisulfite per BI.

Example 9 was prepared in the same manner as Example 6, except that methionine was used instead of catalase as the hydrogen peroxide-neutralizing agent. The methionine (99.00%) was obtained from Calbiochem, EMD Chemicals of Gibbstown, N.J. and was spiked onto the spores at 500 µg per BI.

exact details shown and described, for variations obvious to one skilled in the art will be included within the invention defined by the claims.

All headings are for the convenience of the reader and should not be used to limit the meaning of the text that follows the heading, unless so specified.

Various modifications may be made without departing from the spirit and scope of the invention. These and other embodiments are within the scope of the following claims.

What is claimed is:

1. An article, comprising:
an outer container having an interior volume, a first end comprising an opening, and a second end;
a dry source of measurable biological activity for monitoring a sterilization process disposed in the interior volume;
an effective amount of a dry agent for neutralizing hydrogen-peroxide, the agent being disposed in the interior volume; and
a layer that is permeable to hydrogen peroxide;
wherein both the source of measurable biological activity and the agent are in vapor communication with an environment outside the outer container and the agent,
wherein the layer is interposed between the source of measurable biological activity and the environment outside the outer container,
wherein the article can be used to monitor a sterilization process that includes a hydrogen peroxide sterilization step by subjecting the article to the sterilization process and measuring the effect of the process on the source of biological activity, and wherein the agent protects the source measurable biological activity from detrimental effects of the hydrogen peroxide.

TABLE 4

Different Levels of Various Hydrogen Peroxide-Neutralizing Agents. The data show the number of growth-positive biological indicators for each group tested. With the exception of those designated "NT", four biological indicators were tested per group.

| Example | Concentration of Neutralizing Agent per BI | STERRAD NX 3 min. Half Cycle | STERRAD NX Std Cycle | OPTREOZ $H_2O_2$ only | OPTREOZ Cycle 2 |
|---|---|---|---|---|---|
| Ref. Ex. 6 | 0 (Control) | 0/4 | 0/4 | 0/4 | 0/4 |
| Ex. 6-1 | 4 µg Catalase | 0/4 | 0/4 | 0/4 | 0/4 |
| Ex. 6-2 | 20 µg Catalase | 4/4 | 0/4 | 4/4 | 0/4 |
| Ex. 6-3 | 50 µg Catalase | 4/4 | 4/4 | 4/4 | 4/4 |
| Ex. 6-4 | 100 µg Catalase | 4/4 | 4/4 | 4/4 | 3/4 |
| Ex. 7-1 | 20 µg $Na_2S_2O_3$ | 0/4 | 0/4 | 4/4 | 0/4 |
| Ex. 7-2 | 100 µg $Na_2S_2O_3$ | 4/4 | 2/4 | 4/4 | 0/4 |
| Ex. 7-3 | 200 µg $Na_2S_2O_3$ | 4/4 | 3/4 | 4/4 | 0/4 |
| Ex. 7-4 | 2000 µg $Na_2S_2O_3$ | 4/4 | 4/4 | NT | NT |
| Ex. 8-1 | 20 µg $HNaO_3S$ | 2/4 | 0/4 | 0/4 | 3/4 |
| Ex. 8-2 | 200 µg $HNaO_3S$ | 4/4 | 4/4 | 0/4 | 0/4 |
| Ex. 8-3 | 250 µg $HNaO_3S$ | 4/4 | 4/4 | 1/4 | NT |
| Ex. 8-4 | 2500 µg $HNaO_3S$ | 4/4 | 4/4 | 4/4 | NT |
| Ex. 9 | 500 µg Methionine | 4/4 | 0/4 | 0/4 | NT |

NT = Not tested

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the 2. The article of claim 1, further comprising a closure;
wherein the closure is coupled to the outer container and forms a passageway for vapor or plasma from the environment outside the outer container to pass into the interior volume;
wherein the layer is coupled to the closure.

3. The article of claim 1, wherein the source of measurable biological activity comprises an enzyme activity or a microorganism capable of reproducing.

4. The article of claim 1, wherein a portion of the source of measurable biological activity is disposed in a first coating.

5. The article of claim 4, wherein the article further comprises a first substrate, wherein the first coating is disposed on the first substrate.

6. The article of claim 1, wherein the agent is selected from a group consisting of catalase, a thiosulfate salt, a bisulfite salt, and L-methionine.

7. The article of claim 1 wherein a portion of the agent is disposed in a second coating.

8. The article of claim 7, wherein the article further comprises a second substrate, wherein a portion of the second coating is disposed on the second substrate.

9. The article of claim 7, wherein the second coating is proximate the first coating.

10. The article of claim 1, further comprising an indicator capable of reacting with the source of measurable biological activity.

11. The article of claim 1, wherein the layer is coupled to the outer container.

12. A method, comprising:
processing the article of claim 1 using a process that comprises:
placing the article in a sterilization chamber;
introducing into the chamber a first quantity of a first sterilant, wherein the first quantity of first sterilant is suspected of comprising an effective amount of hydrogen peroxide;
exposing the article to the first sterilant for a period of time; and
detecting the measurable biological activity.

13. The method of claim 12, further comprising:
introducing into the chamber a second quantity of a second sterilant; and
exposing the article to the second sterilant for a period of time.

14. The method of claim 13, wherein the second quantity of second sterilant is suspected of comprising hydrogen peroxide, wherein the second quantity is introduced into the chamber at a predetermined time after the first quantity is introduced into the chamber.

15. The method of claim 13, wherein the second quantity of second sterilant is suspected of comprising an effective amount of a sterilant other than hydrogen peroxide.

16. The method of claim 15, wherein the second quantity is introduced into the chamber after the first quantity is introduced into the chamber.

17. The method of claim 12, wherein detecting the measurable biological activity comprises detecting an enzyme activity or detecting a pH change.

* * * * *

UNITED STATES PATENT AND TRADEMARK OFFICE
CERTIFICATE OF CORRECTION

PATENT NO.      : 9,675,722 B2
APPLICATION NO. : 14/770218
DATED           : June 13, 2017
INVENTOR(S)     : Francois Ahimou It is certified that error appears in the above-identified patent and that said Letters Patent is hereby corrected as shown below:

On the Title Page

Page 2, Column 2 (Other Publications)
Line 11, delete "subtillis" and insert -- subtilis --, therefor.

In the Specification

Column 1
Line 9 (approx.), delete "371" and insert -- §371 --, therefor.

Column 3
Line 41, after "peroxide" insert -- . --.

Column 4
Line 6-7, delete "glutaraldehye," and insert -- glutaraldehyde, --, therefor.

Column 8
Line 3, delete "polypropylene-," and insert -- polypropylene, --, therefor.
Line 32, after "2" insert -- . --.

Column 15
Lines 29-33, delete "VHP" and insert -- HPV --, therefor.

Signed and Sealed this
Twelfth Day of December, 2017

Joseph Matal
*Performing the Functions and Duties of the
Under Secretary of Commerce for Intellectual Property and
Director of the United States Patent and Trademark Office*